US008579868B2

(12) United States Patent
Christiansen

(10) Patent No.: US 8,579,868 B2
(45) Date of Patent: Nov. 12, 2013

(54) MEDICAL DELIVERY SYSTEM WITH FLEXIBLE BLOCKING ELEMENT

(75) Inventor: Asger Voss Christiansen, Guldborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 207 days.

(21) Appl. No.: 12/374,600

(22) PCT Filed: Jul. 15, 2007

(86) PCT No.: PCT/EP2007/057284
§ 371 (c)(1),
(2), (4) Date: Mar. 19, 2009

(87) PCT Pub. No.: WO2008/009647
PCT Pub. Date: Jan. 24, 2008

(65) Prior Publication Data
US 2009/0259197 A1 Oct. 15, 2009

Related U.S. Application Data

(60) Provisional application No. 60/837,828, filed on Aug. 14, 2006.

(30) Foreign Application Priority Data

Jul. 15, 2006 (EP) .................................... 06014769
Aug. 14, 2006 (EP) .................................... 06118846

(51) Int. Cl.
*A61M 5/00* (2006.01)
(52) U.S. Cl.
USPC ........... 604/211; 604/207; 604/208; 604/209; 604/210; 604/135

(58) Field of Classification Search
USPC .......................................... 604/135, 207–211
See application file for complete search history.

(56) References Cited

U.S. PATENT DOCUMENTS

| 31,873 A | 4/1861 | Cramer |
| 31,878 A | 4/1861 | Downer |

(Continued)

FOREIGN PATENT DOCUMENTS

| CH | 0315980 | 9/1956 |
| CH | 0501411 | 1/1971 |

(Continued)

OTHER PUBLICATIONS

English Abstract of DE20110690 from *Derwent Innovation Index* (corresponds to DE20110690 above).

(Continued)

*Primary Examiner* — Kevin C Sirmons
*Assistant Examiner* — Edelmira Bosques
(74) *Attorney, Agent, or Firm* — Wesley A. Nicolas; Marc A. Began; Reza Green

(57) ABSTRACT

A medical delivery system (200) having a container (202) and a dosing assembly (204), where the container is fastenable to the dosing assembly by a movement comprising a translatory movement followed by a rotational movement. One of the container and the dosing assembly comprises one or more blocking elements (207) movable between a blocking position and a non-blocking position responsive to the rotational movement. Each blocking element is able to engage the other one of the container and the dosing assembly. A container suitable for use in said medical delivery system.

23 Claims, 9 Drawing Sheets

(56) References Cited

U.S. PATENT DOCUMENTS

Figure 1:
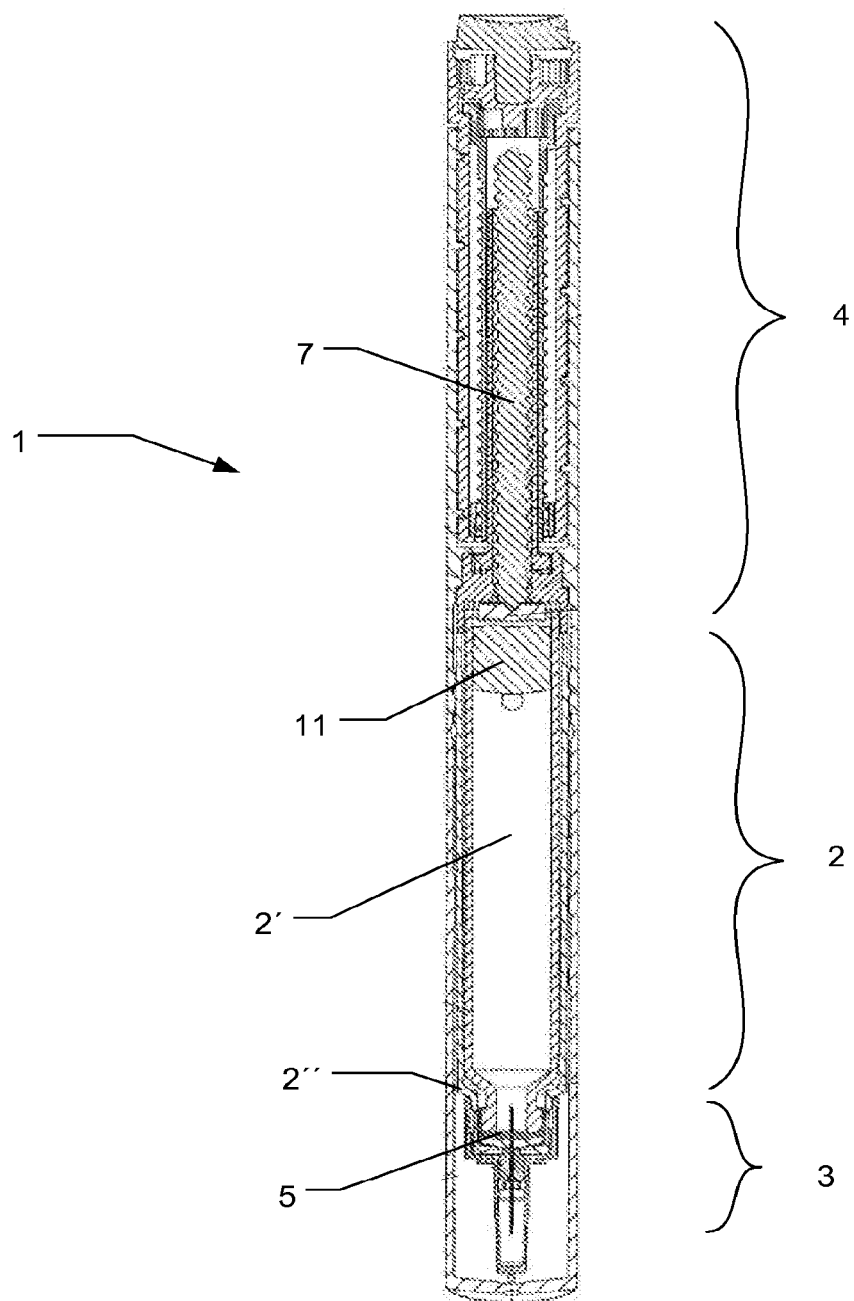

| | | |
|---|---|---|
| 1,594,493 A | 8/1926 | Brown |
| 2,020,828 A | 11/1935 | Goldberg |
| 2,707,466 A | 5/1955 | Hoskins |
| 2,818,864 A | 1/1958 | Hudson |
| 2,865,372 A | 12/1958 | Miskel et al. |
| 2,880,723 A | 4/1959 | Adams |
| 2,888,924 A | 6/1959 | Dunmire |
| 3,021,840 A | 2/1962 | Hallamore et al. |
| 3,130,724 A | 4/1964 | Higgins et al. |
| 3,130,742 A | 4/1964 | Higgins et al. |
| 3,170,667 A | 2/1965 | Szohatzky |
| 3,336,924 A | 8/1967 | Sarnoff et al. |
| 3,375,825 A | 4/1968 | Keller |
| 3,820,652 A | 6/1974 | Tiiackston |
| 3,831,599 A | 8/1974 | Needham |
| 3,895,633 A | 7/1975 | Bertner et al. |
| 3,916,893 A | 11/1975 | De Felice |
| 3,989,044 A | 11/1976 | Meierhoefer |
| 4,089,432 A | 5/1978 | Crankshaw |
| 4,150,673 A | 4/1979 | Watt |
| 4,280,723 A | 7/1981 | Moldestad |
| 4,490,142 A | 12/1984 | Silvern |
| 4,592,745 A | 6/1986 | Rex et al. |
| 4,619,640 A | 10/1986 | Potolsky et al. |
| 4,619,651 A | 10/1986 | Kopfer et al. |
| 4,664,656 A | 5/1987 | Taddei |
| 4,685,314 A | 8/1987 | Greenwalt et al. |
| 4,693,833 A | 9/1987 | Toshikuni et al. |
| 4,740,205 A | 4/1988 | Seltzer |
| 4,768,568 A | 9/1988 | Fournier et al. |
| 4,781,701 A | 11/1988 | Geprags |
| 4,944,736 A | 7/1990 | Holtz |
| 4,948,000 A | 8/1990 | Grobenkort |
| 4,973,318 A | 11/1990 | Holm et al. |
| 4,976,701 A | 12/1990 | Ejlersen et al. |
| 5,000,744 A | 3/1991 | Hoffman et al. |
| 5,002,537 A | 3/1991 | Hoffman et al. |
| 5,017,190 A | 5/1991 | Simon et al. |
| 5,084,017 A | 1/1992 | Maffetone |
| 5,205,833 A | 4/1993 | Harsh et al. |
| 5,226,896 A | 7/1993 | Harris |
| 5,244,465 A | 9/1993 | Michel |
| 5,269,317 A | 12/1993 | Bennett |
| 5,286,258 A | 2/1994 | Haber et al. |
| 5,458,580 A | 10/1995 | Hajishoreh |
| 5,478,323 A | 12/1995 | Westwood et al. |
| 5,498,253 A | 3/1996 | Aswad et al. |
| 5,554,134 A | 9/1996 | Bonnichsen |
| 5,584,815 A | 12/1996 | Pawelka et al. |
| 5,611,783 A | 3/1997 | Mikkelsen |
| 5,693,027 A | 12/1997 | Hansen et al. |
| 5,743,889 A | 4/1998 | Sams |
| 5,938,642 A | 8/1999 | Burroughs et al. |
| 5,954,700 A | 9/1999 | Kovelman |
| 5,957,896 A * | 9/1999 | Bendek et al. ............... 604/207 |
| 6,017,330 A | 1/2000 | Hitchins et al. |
| 6,197,040 B1 | 3/2001 | LaVaughn et al. |
| 6,582,399 B1 | 6/2003 | Smith et al. |
| 6,582,408 B1 | 6/2003 | Buch-Rasmussen et al. |
| 6,648,859 B2 | 11/2003 | Bitdinger et al. |
| 7,604,619 B2 | 10/2009 | Eich et al. |
| 2001/0047153 A1 | 11/2001 | Trocki et al. |
| 2002/0016571 A1 | 2/2002 | Kirchhofer et al. |
| 2002/0099360 A1 | 7/2002 | Bierman |
| 2002/0169470 A1 | 11/2002 | Kuhr et al. |
| 2003/0004466 A1 | 1/2003 | Bidtinger et al. |
| 2003/0078195 A1 | 4/2003 | Kristensen et al. |
| 2004/0210199 A1 | 10/2004 | Atterbury |
| 2004/0215152 A1 | 10/2004 | Kirchhofer et al. |
| 2004/0238776 A1 | 12/2004 | Peters et al. |
| 2006/0153693 A1 * | 7/2006 | Fiechter et al. ............... 417/63 |
| 2008/0051713 A1 | 2/2008 | Kohlbrenner |
| 2010/0004603 A1 | 1/2010 | Kristensen et al. |
| 2010/0030158 A1 | 2/2010 | Christiansen |

FOREIGN PATENT DOCUMENTS

| | | |
|---|---|---|
| DE | 2137405 | 2/1973 |
| DE | 44 19 235 | 12/1995 |
| DE | 20110690 | 9/2001 |
| EP | 217055 | 4/1987 |
| EP | 549 694 | 7/1993 |
| EP | 549694 | 6/1995 |
| EP | 762311 | 3/1997 |
| EP | 774270 | 5/1997 |
| EP | 774270 A1 | 5/1997 |
| EP | 832661 A2 | 4/1998 |
| EP | 897729 | 2/1999 |
| EP | 897728 | 5/2003 |
| GB | 301961 | 12/1928 |
| GB | 1205201 | 9/1970 |
| GB | 1437595 | 5/1976 |
| GB | 1525455 | 9/1978 |
| GB | 2 214 819 | 9/1989 |
| WO | WO89/02760 | 4/1989 |
| WO | WO 90/09202 | 8/1990 |
| WO | WO92/04926 | 4/1992 |
| WO | WO98/47559 | 10/1998 |
| WO | WO98/56438 | 12/1998 |
| WO | WO00/02605 | 1/2000 |
| WO | WO 00/35519 | 6/2000 |
| WO | WO 01/72361 | 10/2001 |
| WO | WO 02/30490 | 4/2002 |
| WO | WO 03/011372 | 2/2003 |
| WO | WO 03/011373 | 2/2003 |
| WO | WO03/017915 | 3/2003 |
| WO | 03097131 A1 | 11/2003 |
| WO | WO 2006/069456 | 7/2006 |
| WO | WO 2008/009646 | 1/2008 |

OTHER PUBLICATIONS

Search Report from International Application No. PCT/EP2007/062661, mailed Feb. 25, 2008.
English language translation for CH0315980.
English language translation for CH0501411.
English language translation for DE2137405.
English language translation for DE44 19 235.
Non-Final Office Action Mailed Nov. 18, 2004 in U.S. Appl. No. 10/230,428, filed Aug. 23, 2002; First Named Inventor: Lars Thougaard Kristensen.
Non-Final Office Action Mailed Feb. 9, 2006 in U.S. Appl. No. 10/230,428, filed Aug. 23, 2002; First Named Inventor: Lars Thougaard Kristensen.
Non-Final Office Action Mailed Dec. 12, 2006 in U.S. Appl. No. 10/230,428, filed Aug. 23, 2002; First Named Inventor: Lars Thougaard Kristensen.
Non-Final Office Action Mailed Feb. 10, 2009 in U.S. Appl. No. 11/784,738, filed Apr. 9, 2007; First Named Inventor: Lars Thougaard Kristensen.
Final Office Action Mailed Jun. 2, 2009 in U.S. Appl. No. 11/784,738, filed Apr. 9, 2007; First Named Inventor: Lars Thougaard Kristensen.
Non-Final Office Action Mailed Jan. 19, 2010 in U.S. Appl. No. 12/373,339, filed Jan. 12, 2009; First Named Inventor: Michael Ejstrup Hansen.

* cited by examiner

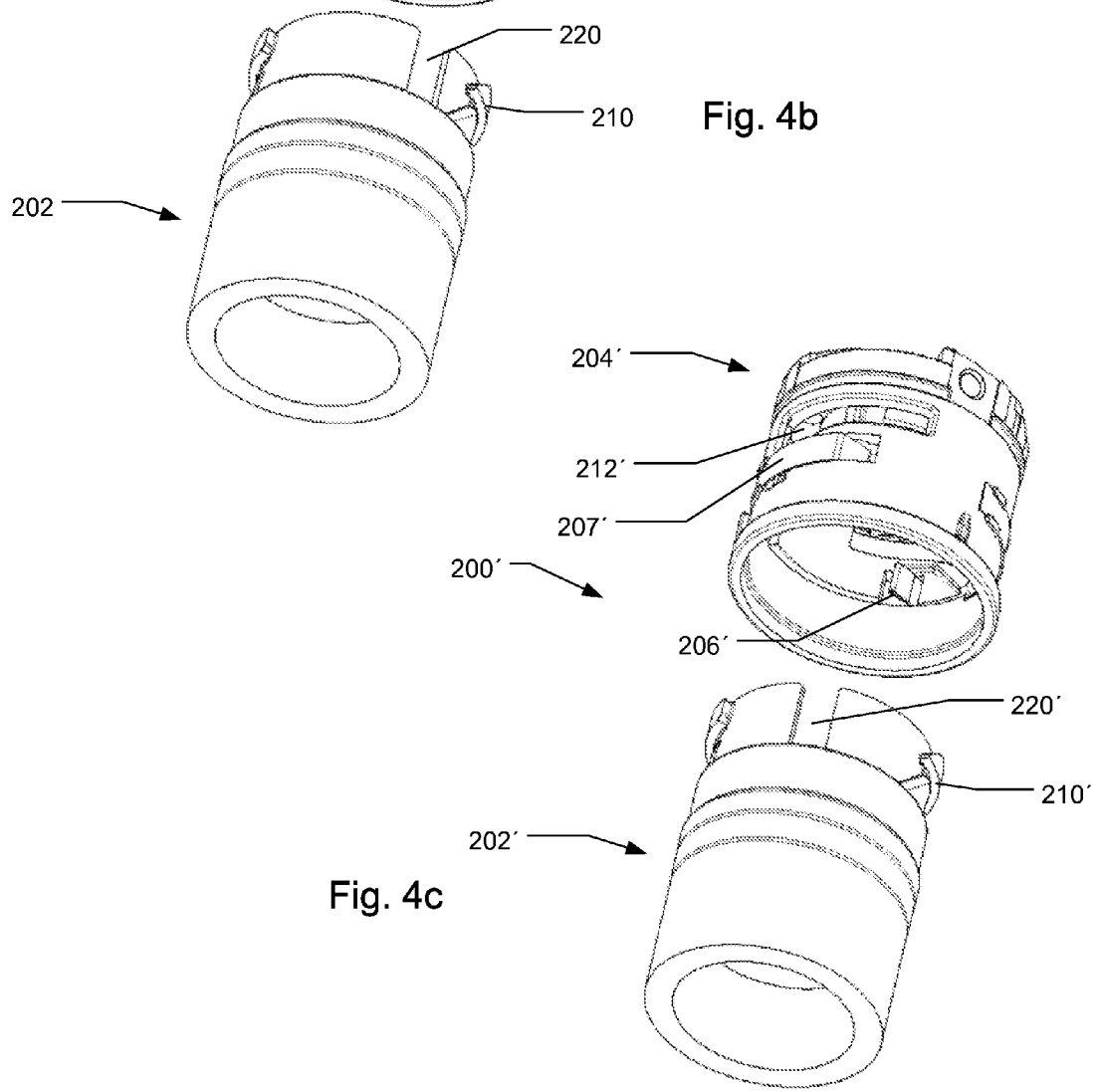

MEDICAL DELIVERY SYSTEM WITH FLEXIBLE BLOCKING ELEMENT

CROSS-REFERENCE TO RELATED APPLICATIONS

This application is a 35 U.S.C. §371 national stage application of International Patent Application PCT/EP2007/057284 (published as WO 2008/009647), filed Jul. 15, 2007, which claimed priority of European Patent Applications 06014769.1, filed Jul. 15, 2006 and 06118846.2, filed Aug. 14, 2006; this application further claims priority under 35 U.S.C. §119 of U.S. Provisional Application 60/837,828, filed Aug. 14, 2006.

FIELD OF THE INVENTION

The present invention relates to a medical delivery system comprising a container and a dosing assembly. In particular the present invention relates to a medical delivery system wherein one of the container and the dosing assembly comprises a flexible blocking element adapted to engage the other one of the container and the dosing assembly. Furthermore, the present invention relates to a container and a dosing assembly each of which are suitable for use in the medical delivery system according to the present invention.

BACKGROUND OF THE INVENTION

Generally, in order to provide superior medication delivery devices which are likely to be well received by particular groups of patients, a greater diversity in drug delivery systems have been launched to the benefit of patients. As the number of commercially available delivery systems increase, numerous different types of medication holding cartridges or containers are distributed. Most of these types of containers differ in various aspects.

Each medicament container may be filled with a particular type of medicament selected from a large variety of different medicaments, but also different kinds of the same class of medicament (e.g. rapid or long acting insulin) and different concentrations of each particular medicament may be accommodated in the containers.

Moreover, different container volumes may be introduced in order to customize each container, and, thus, the delivery system to the needs of particular users. Variation of container volume may be provided by changing the length or diameter of the container. These modifications usually imply corresponding modifications of the dosing assembly of a medication delivery system, so as to provide a particular stroke of a driving element for expelling the medicament from the container or to provide optimal dosing precision. Further discrimination between different medicament containers may be occasioned by the design requirements for each particular delivery system, such as required sliding friction of the piston accommodated in the container.

In order to discriminate between a larger variety of available containers, numerous container coding systems have been developed which primarily relies on the electronic reading and recognition of specific containers in order to allow delivery of a specific type of a medicament by a dedicated delivery device. The following mechanical coding systems are known in the art:

U.S. Pat. No. 5,611,783 relates to a pen shaped syringe comprising a distal part which may comprise an ampoule and a proximal part containing a dose setting and drive mechanism. The proximal and distal parts have interlocking bayonet coupling means. Protrusions may be provided to form a pattern ensuring that a certain distal part may only be used in connection with a certain proximal part.

WO 03/017915 A1 discloses a cartridge having a distal end provided with a mechanical coding. The mechanical coding has the form of a circular protrusion where the circular outer diameter is dedicated a specific concentration of insulin contained in the cartridge.

U.S. Pat. No. 5,693,027 discloses a plastic top for adapting a standard cartridge to a chosen syringe. The plastic top may be provided with means for keyed engagement with corresponding means in a syringe to keep it unrotable when mounted with a cartridge in the syringe. In some types of syringes such keyed engagement between cartridge and syringe is further used to ensure that only a certain type of cartridge is used.

U.S. Pat. No. 6,648,859 B2 discloses a drug cartridge assembly for use with a reuseable pen body assembly of a medication delivery pen. In order to eliminate cross-use the pen body assembly and the drug cartridge are keyed i.e. they may be threadedly engaged by corresponding threads and grooves, bayonet threads, and grooves, snap fits or a pair of lugs that mate in reverse Luer-Lock manner. The mating members are selected so as to prevent cross-use with other assemblies, e.g., the pitch of the threads may be angled so as to mate only with one another and not with other assemblies.

Yet another prior art system is described in DE 201 10 690.

It is an object of a preferred embodiment of the present invention to provide an alternative to the known systems. Furthermore, it is an object of a preferred embodiment of the present invention to provide a medication delivery system with a large number of possible coding geometries.

Furthermore, it is an object of a preferred embodiment of the present invention to provide a coding system wherein the user experiences substantially the same operational fastening movement when the container and dosing assembly of a predetermined medical delivery system are coupled/uncoupled to each other regardless of the specific choice among sets of compatible container/dosing assemblies. Additionally, it is an object of a preferred embodiment of the present invention to provide a system having a large number of differently coded containers/dosing assemblies while simultaneously obtaining a rugged system where the possibility of mechanical failure is minimized.

Furthermore, it is an object of a preferred embodiment of the present invention to provide an intuitive fastening mechanism for fastening the container to the dosing assembly.

BRIEF DESCRIPTION OF THE INVENTION

In a FIRST aspect the present invention relates to a medical delivery system comprising:
- a container comprising a housing adapted to contain a medicament in a chamber and a slideably arranged piston which is moveable in a distal direction towards an outlet so as to reduce the volume of the chamber and expel the medicament through the outlet;
- a dosing assembly having a container receiving cavity for at least partly receiving the container therein and for coupling the container to the dosing assembly so as to allow driving means of the dosing assembly to move the piston of the container in the distal direction;

wherein the dosing assembly defines a first fastening means adapted to engage a second fastening means of the container so as to fasten the container to the dosing assembly where the fastening movement comprises a relative axial movement along a first axis followed by a relative rotational movement around the first axis;

wherein the dosing assembly comprises one or more blocking elements, where said one or more blocking elements are moveable from a first position where the blocking elements relative to said first axis extends radially into said container receiving cavity and moveable towards a second position where the blocking elements are moved radially outwards, and wherein the blocking elements are moveable from said first position to said second position responsive to said relative rotational movement while being prevented to move from said first position to said second position when acted upon by an axially directed force; and wherein the container comprises a wall part formed with axially extending indentations adapted to receive said predetermined number of blocking elements and which allows the container to be axially inserted into said container receiving cavity.

According to the present invention, different coding variants may be obtained by varying the distribution of the blocking elements and corresponding axially extending indentations along the outline of the coupling parts of the medical delivery system. Thereby it may be ensured that a container of a first medical delivery system is coded such that it cannot be fastened to a dosing assembly of a second medical delivery system. Analogously, it may be ensured that the container of the second medical delivery system is coded such that it cannot be fastened to the dosing assembly of the first medical delivery system. Accordingly, the medical system according to the present invention improves user safety as only predetermined containers may be attached to a specific dosing assembly. Thus, the dosing assembly may be designated to be used with a predetermined kind and/or concentration of a medicament and containers accommodating other concentrations or types of medicaments cannot be attached to the dosing assembly.

The system according to the present invention provides the advantage that dimensions of the coding features as defined by the axially extending indentations can be minimized— even when incorporating a coupling for fastening the container to the dosing assembly following a coupling scheme comprising an axial movement followed by a rotational movement, such as in a bayonet coupling. This provides the possibility of a larger variety of distinct container codings. In addition, since the coding features of the present invention requires less space, the part of the coding system comprising the indentations can be made more robust compared to systems where fixed male coding elements requires large angular mating female openings. According to the invention, devices may be coded by varying the rotational position of one or more of the blocking element and correspondingly varying the rotational position of corresponding one or more indentations. However, the overall specific user interface for coupling and uncoupling a container from a dosing assembly may be kept identical even for differently coded systems. This is especially beneficial for users that regularly uses several different coded delivery systems for administering different kinds of medicaments.

In the context of the present invention the term "medical delivery system" shall be understood as any system capable of administering a medicament-containing flowable drug.

Examples of medical delivery systems are infusion pump applications, dosers, pen-shaped dosers, motor-dosers, and automated syringes such as the AutoPen™.

The invention is applicable to all kinds of medicament delivery devices capable of delivering a medicament to a user from a container which is adapted to be coupled to a dosing assembly of the delivery device. The delivery device may include any delivery device for transcutaneous, subcutaneous, intravenous, intra muscular or pulmonary administration of a drug.

As used herein, the term "medicament" is meant to encompass any medicament-containing flowable drug capable of being passed through a delivery means such as a hollow needle or canula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The chamber or reservoir of the container may defined by one or more sidewalls of the container housing and the slidably arranged piston. In most embodiments at least a part of the container is ring-shaped and defines a cylindrical cavity in which the piston is received. The distal end of the container may comprise a seal for penetration by a cannula so as to allow a medicament contained in the chamber to be expelled through delivery means such as through a cannula or through a tubing. The distal end of the container may be adapted to be attached to a holder holding a cannula. As an example the distal end of the container may comprise a thread adapted to cooperate with a corresponding thread of the holder so as to allow the holder to be screwed onto the container. Alternatively, the distal end of the container may be adapted to couple to an infusion set.

The outlet of the container may be adapted to cooperate with or be defined by a cannula or a needle or a needle hub or an infusion set, or any other fluid communicating conduit adapted to provide fluid access to a medicament accommodated in the container.

The driving means of the dosing assembly may comprise a piston rod adapted to move the piston in the distal direction. The piston rod may comprise an element which is more rigid than the piston and is adapted to abut at least a part of and preferably most of the proximal facing surface of the piston whereby a force applied by the piston rod to the rigid element is applied to a larger area of the proximal surface of the piston than if the piston rod had engaged the piston directly. The piston rod may be adapted to transfer a driving force to the piston either directly or via other parts situated in the dosing assembly and/or in the container.

The dosing assembly defines a first fastening means which during fastening of the container to the dosing assembly engages a second fastening means of the container. In one embodiment a proximal facing surface of the first fastening means of the dosing assembly engages a distal facing surface of the second fastening means of the container.

The coupling scheme for coupling the container to the dosing assembly may comprise a concurrent axial and rotational movement, such as a helical movement. The rotational movement incurred by the concurrent axial and rotational movement is less than one revolution, such as less than 120 degrees, such as less than 90 degrees, such as less than 60 degrees, such as less than 30 degrees, such as less than 20 degrees. When the proximal facing surface of the first fastening means and the distal facing surface of the second fastening means are brought into engagement, rotation of the container relative to the dosing assembly may cause the container and the dosing assembly to be pulled towards each other.

In a first embodiment the first fastening means of the dosing assembly defines a groove adapted to receive a projection or male member defined by the second fastening means of the container. During fastening of the container to the dosing assembly, a substantially proximal facing surface of the first fastening means of the dosing assembly engages a substantially distal facing surface of the container. The predetermined movement is defined by the shape of at least one of the engaging surfaces. In a further embodiment the second fastening means defines a plurality of projections such as two, three or four, and the first fastening means defines a corresponding plurality of grooves adapted to be engaged by the projections.

In a second embodiment the groove(s) is/are defined by the container and the projection(s) is/are defined by the dosing assembly. In a third embodiment the container defines a combination of grooves and projections adapted to be engaged by corresponding projections and grooves defined by the dosing assembly.

In the context of the present invention the terms "groove" and "projection" are only used in connection with the first and second fastening means, and "indentation" and "protrusion" are only used in connection with engaging/receiving mechanism of the rotatable element and the second part extending coding mechanism. However, "groove", "indentation" and "female member" shall be seen as synonyms and "protrusion", "projection" and "male member" shall be seen as synonyms.

The first and second fastening means may be adapted to engage in a releasable or permanent manner. Even when the fastening means are adapted to engage by a permanent engagement, the invention provides increased safety against mix-up prior to the final assembling of the medical delivery device, e.g. during fabrication.

In one embodiment the number of blocking elements are selected as one, two, three, four or five) each of which may be adapted to engage a corresponding/mating/matching indentation of the second part. However, the main purpose of the blocking elements is to prevent or limit the axial entry of a container into a container receiving cavity of the dosing assembly. The terms "corresponding/mating/matching" above does not necessarily mean a form fitting engagement, i.e. the indentations may be much wider (in the peripheral direction) than the blocking elements.

In one embodiment the indentations are wider (circumferentially) than the blocking elements, and, thus, the blocking elements are allowed to move rotationally inside the indentations, whereby the second part will be allowed to rotate relative to the rotatable element when the protrusions are received in the indentations without moving the blocking elements from their first position to their second position.

In other embodiments, the blocking element(s) and the indentation(s) may have substantially the same circumferential width. Alternatively, the blocking element(s) may be slightly wider than the indentation(s).

In one embodiment the first and second fastening means, and the blocking elements and the indentations are arranged such that the first and second fastening means must at least partly engage in order for the blocking element to be received in the indentation. In other words when fastening the container to the dosing assembly, the blocking elements cannot be received in the indentation(s), if not the projection(s) (of the first or second fastening means) are at least partly received in the groove(s) (of the other of said first or second fastening means).

In one embodiment the dosing assembly defines the one or more blocking elements. In some embodiments the blocking elements protrudes into a container receiving cavity for blocking axial entry of non-allowed containers. In other embodiments, the blocking element protrudes radially outwards for blocking the coupling of a non-allowed dosing assembly into a form-fitting container having a cavity for receiving at least a part of the dosing assembly therein. In still other embodiments, the blocking elements are defined by the container, where the blocking elements protrudes radially into or outwards from a container wall. In these embodiments, the dosing assembly are provided with axially extending indentations for coding to a correct container.

Still other embodiments include medical delivery devices where both the container and the dosing assembly are provided with each one or more blocking elements to be received in corresponding axially extending indentation(s) of the other part.

In one embodiment, the delivery system comprises two or more blocking elements. The two or more blocking elements may be arranged at irregular mutual distances, e.g. to provide a non-symmetrical coding system arranged around a circumferential portion of the coupling interface.

In one embodiment, the container comprises second fastening means arranged at a distance $X_1$ from the proximal end of the container. The second fastening means may be provided by male members for cooperating with female members of the dosing assembly. An axial extent of a male member may be designated a thickness $t_1$. In such a system, the one or more indentations exceeds the distance $X_1+t_1$. In specific embodiments, the distance that said one or more indentations extends in the distal direction exceeds $X_1+t_1$ such as by 50%, such as by 75%, such as by 100%, such as by 150%, such as by 200% and such as by 300%.

In some embodiments the second fastening means are arranged at the extreme proximal end of the container.

In one embodiment, the one or more indentations are formed as longitudinally indentations which are recessed compared to neighbouring sections. In such a configuration, the indentations may be provided as a reduced thickness of a wall portion of the container. In other embodiments, the container provides a central cavity arranged in the end face of the proximal end of the container where the indentations extends radially from the central cavity of the container and radially outwards to the container exterior. Thereby the indentations may form openings defined in a side wall of the container.

In one embodiment the container comprises a cartridge holder and a cartridge defining said chamber. The second fastening means may be defined by or attached to the cartridge holder. Moreover, the indentation(s)/blocking element(s) may be defined by the cartridge holder. The cartridge and the cartridge holder may be two separate elements, and the cartridge may be frictionally retained in the cartridge holder. In one embodiment the cartridge is made of glass and the cartridge holder is made of a non-glass material for protecting the glass cartridge. The cartridge may be non-removably retained in the cartridge holder so as to resist tampering. Even if such a cartridge is removed from the cartridge holder it cannot be reattached by hand and without tools. This provides the advantage that the cartridge holder cannot be reused when the cartridge has been emptied, accordingly a cartridge with a wrong medicament cannot be inserted into the cartridge holder and be dispensed by use of the dosing assembly. The cartridge holder and the cartridge may define a monolithic element, i.e. forming a one element without seams. Such a monolithic element may be formed as a molded article made of a synthetic resin such as cyclic olefin copolymer, e.g. Topas® or made of polypropylene. However, any material which is suitable for long-term storage of the specific medication to be accommodated in the container may be used.

In one embodiment, the second fastening means are associated with the proximal end of the container. In other embodiments, the second fastening means are associated at a position extending from the proximal end of the container by a given distance, such as midway between the proximal and distal ends or even closer to the distal end of the container. In still other embodiments, the second fastening means are associated with the distal end of the container.

In one embodiment, the one or more indentations extends from the proximal end of the container. In still other embodiments, the indentations extends from a side wall portion of the container distant from the proximal end and extending further towards the distal end. As describe in above at least a part of said predetermined movement may be a concurrent axial and rotational movement. Moreover, at least one of:
  the first and second fastening means, and
  the blocking elements(s) and/or indentation(s) of each of the rotatable element and the second part,
may be adapted to prevent a part of the axial and/or rotational movement of the predetermined movement, so as to prevent coupling of the container to the dosing assembly, unless:
  each of the first and second fastening means defines a predetermined coding geometry, and/or
  each of the blocking elements(s) and/or indentation(s) defines a predetermined coding geometry.
  Moreover, the coding geometry of:
  one or more of the first and/or second fastening means, and/or
  one or more of the blocking element(s) and/or indentation(s),
may be defined by at least one of: a circumferential extent of the first and second fastening means, an axial extent of the first and second fastening means, a radial extent of the first and second fastening means and the circumferential position of the first and second fastening means.

Accordingly, it will be appreciated that the medical delivery system according to the present invention provides a plurality of coding geometries each of which may be used to designate different features. As an example the first and second fastening means may be used to designate a first predetermined feature of the medicament such as its kind, and the rotational position of the blocking elements may be used to designate a second predetermined feature of the medicament such as its concentration. Other examples of features which may be designated by a coding geometry are: male/female medication; child/adult medication; prophylactic/therapeutic medication, slow/fast acting medication.

Alternatively, the first and second fastening means, and the rotational position of the blocking elements may be redundant such that if one of them fails, the other one will ensure that only predetermined containers and dosing assemblies can be fastened to each other. Accordingly, an extra level of security is provided due to the two redundant coding geometries.

One embodiment comprises:
  a first container having any of the abovementioned features and/or elements, which first container is adapted to be fastened to a first dosing assembly having any of the abovementioned features and/or elements; and
  a second container having any of the abovementioned features and/or elements, which second container is adapted to be fastened to a second dosing assembly having any of the abovementioned features and/or elements; and wherein at least one of:
  the first fastening means of the dosing assemblies,
  the second fastening means of the containers, and
  each of the blocking elements(s) and/or indentation(s),
are adapted to prevent the first dosing assembly and second container from being fastened to each other, and to prevent the second dosing assembly and the first container from being fastened to each other.

Moreover, the predetermined movement required for coupling and uncoupling the first container to the first dosing assembly and for coupling the second container to the second dosing assembly may be essentially the same.

In a SECOND aspect the present invention relates to a container suitable for use (adapted to be used) in a medical delivery system according to the first aspect of the invention.

It will be appreciated that the invention according to the second aspect may comprise any feature and/or element of the invention according to the first aspect. In particular the container of the second aspect may comprise any feature and/or element of the container according to the first aspect of the invention.

In a THIRD aspect the present invention relates to a dosing assembly suitable for use (adapted to be used) in a medical delivery system according to the first aspect of the invention.

It will be appreciated that the invention according to the third aspect may comprise any feature and/or element of the invention according to the first aspect. In particular the dosing assembly of the third aspect may comprise any feature and/or element of the dosing assembly according to the first aspect of the invention.

DETAILED DESCRIPTION OF THE INVENTION

Figure 2:
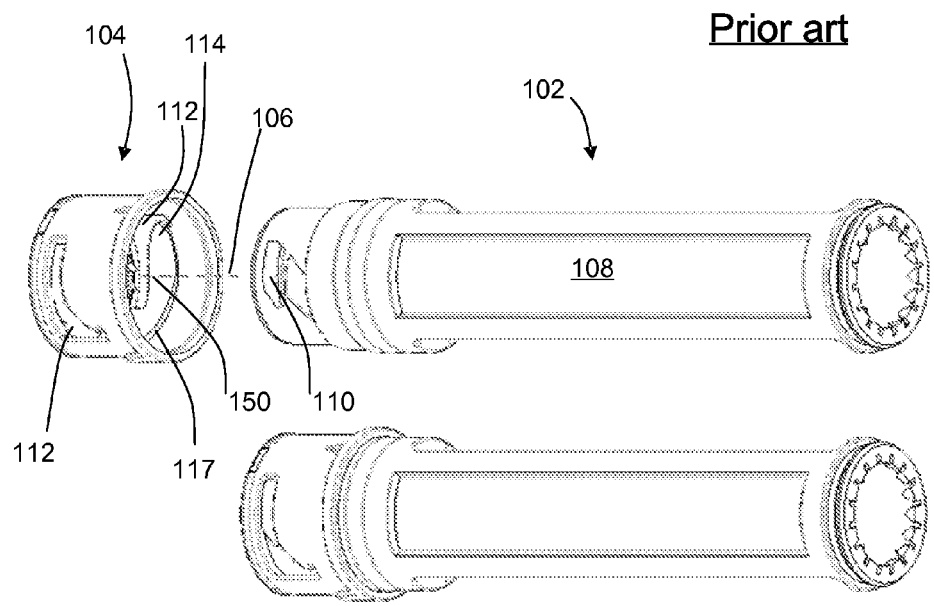
Figure 3:
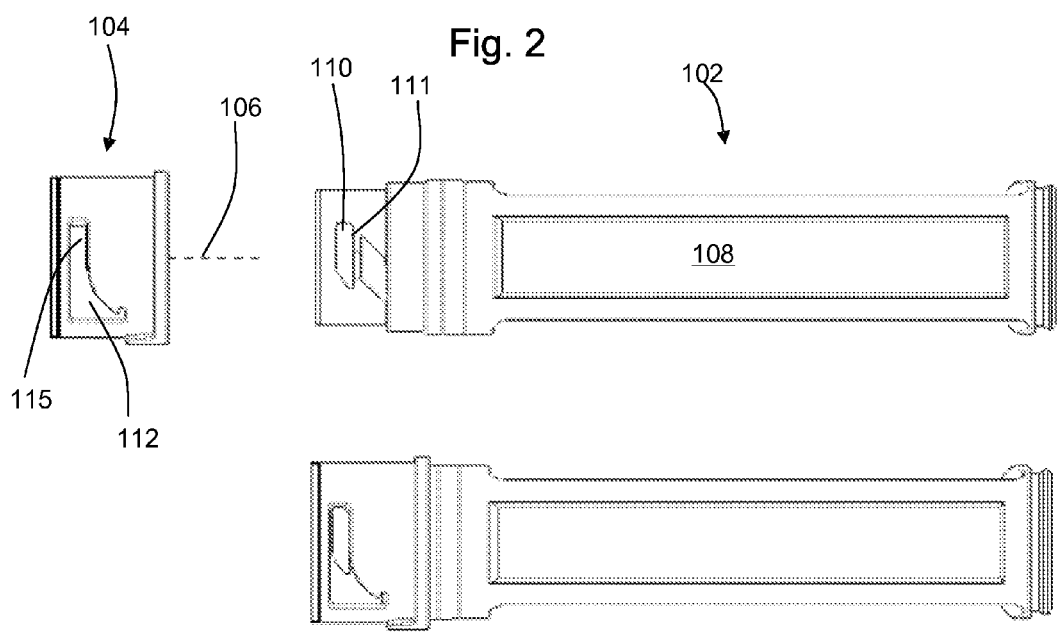
Figure 4A:
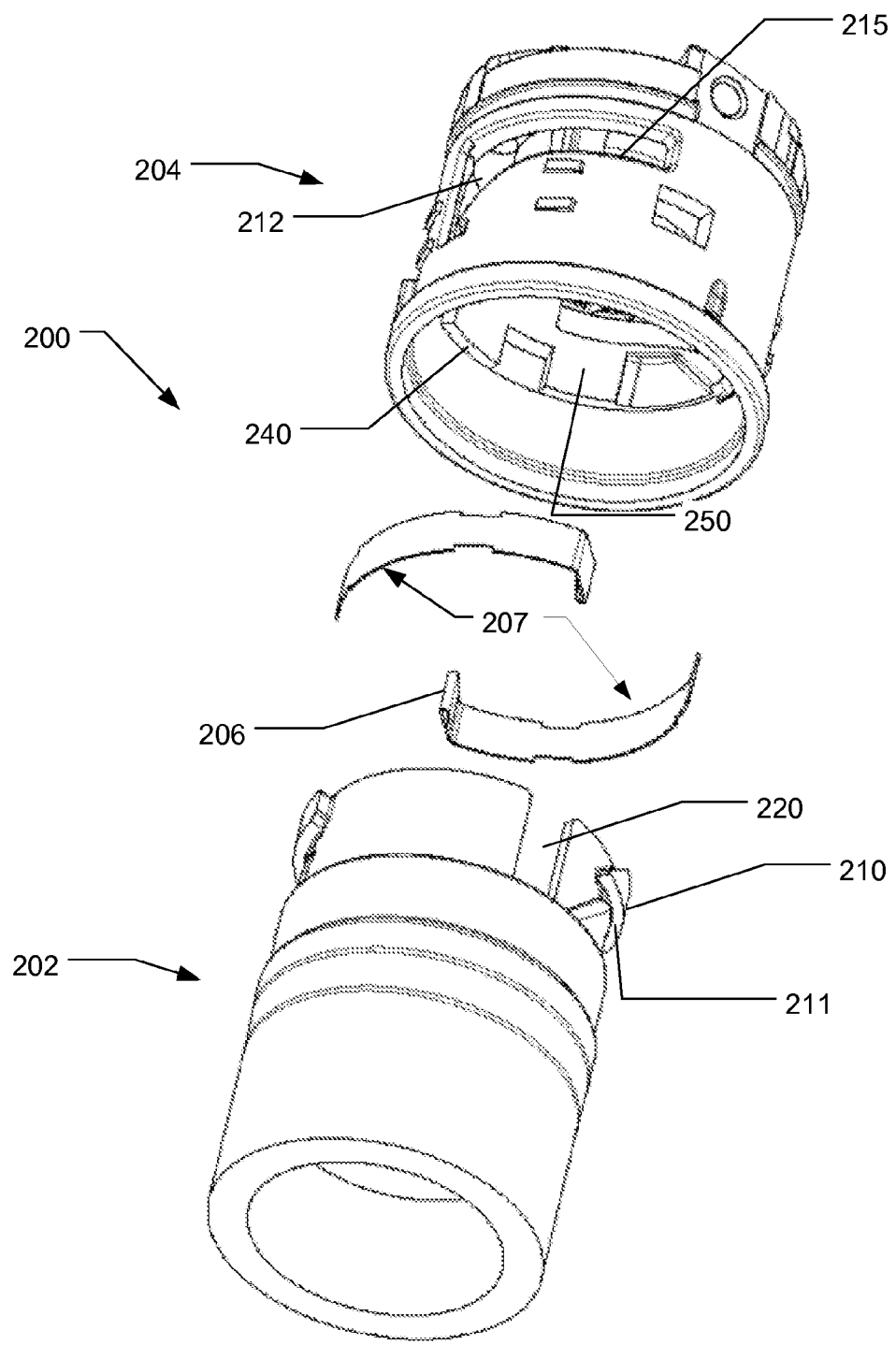

The invention will now be described in further detail with reference to the drawings in which:
  FIG. 1 shows a prior art medical delivery system,
  FIGS. 2 and 3 show a prior art container coupling system,
  FIGS. 4a, 4b, 4c show two specific container coupling systems according to a first embodiment of the present invention,
  FIG. 5 discloses a container coupling system according to a second embodiment of the invention,
  FIG. 6a discloses a container coupling system according to a third embodiment of the invention,
  FIGS. 6b and 6c disclose two alternative container designs according to the third embodiment of the invention,
  FIGS. 7a, 7b, 7c, 7d and 7e disclose a container coupling system according to a fourth embodiment of the invention, and
  FIGS. 8a and 8b shows a container coupling system according to a fifth embodiment of the invention.

FIG. 1 discloses a medical delivery system forming an injection pen 1 comprising a medicament filled container part 2 which is adapted to be secured to a dosing assembly 4. In the depicted form, the dosing assembly 4 forms a mechanism for setting and injecting specific doses of a medicament from the container 2. The container 2 comprises an open distal part which is sealed by a piercable sealing member 5. The container further comprises a slideably mounted piston 11 which is adapted to slide towards the distal part of the container 2 when a force is exerted on the piston 11 in the distal direction. Typically, medication is delivered through a needle cannula 3 which may be releasably secured to the distal part of the container 2. When the container 2 is coupled to the dosing assembly 4, a force exerted by driving means 7 of the dosing assembly is transferred to the piston 11 whereby the medicament contained in the container 2 is expelled through needle 3.

In the depicted form, the container 2 is defined by a cartridge holder 2" adapted to receive a medicament containing cartridge 2', e.g. a standard glass cartridge. The container 2 is provided with fastening means (not shown) for fastening the container 2 to the dosing assembly 4 of the injection pen.

The fastening means of the container 2 is adapted for engaging fastening means of the dosing assembly 4 and the coupling may provide a permanent coupling which renders cartridge removal impossible, thereby forming a prefilled pen which may be disposed off after medicament contained in the cartridge has been emptied.

Alternatively, the fastening means of the container 2 and the fastening means of the dosing assembly 4 may form a releasable connection which then provides the possibility of reusing the dosing assembly with a new container after a previous empty container has been disposed off.

In accordance with the general delivery device concept outlined above, a recent state of the art syringe device has been marketed by the applicant as "NovoPen® 4". This device provides a durable dosing assembly which is adapted to accept disposable medication cartridges which can be easily exchanged by a user. The specific coupling mechanism for coupling a cartridge holder to the dosing assembly of the NovoPen® 4 offers a simple, intuitive and reliable coupling. FIGS. 2 and 3 shows detailed representations of selected parts of the NovoPen® 4 related to the coupling of the cartridge holder to the dosing assembly. The syringe device 100 of FIGS. 2 and 3 comprises a proximal part 104 and a distal part 102. In use, the proximal part 104 forms part of a dosing assembly which comprises driving means (not shown) for expelling minute quantities from syringe device 100. The driving means of the proximal part 104 comprises a piston rod (not shown) extending through a cartridge receiving cavity 150 of the proximal part 104 along a central axis 106. In use, the distal part 102 forms part of a container having a housing 102 for accommodating a reservoir such as a medicament cartridge (not shown). Further, the distal part 102 may be adapted to support or connect to a needle assembly (not shown) at the distal end of distal part 102.

The distal part 102 comprises two male members or projections 110 arranged on each side of the distal part 102. These projections 110 are used to secure the distal part 102 to the proximal part 104, by advancing the projections 110 into matching tracks forming grooves 112 of the proximal part 104. The grooves 112 are defined inside the cartridge receiving cavity 150 on an inner surface of the proximal part 104. The specific shape of each of the grooves 112 are defined by neighbouring ramp shaped ridges 114 protruding radially into the cartridge receiving cavity 150. Each of the grooves are defined by a first part having an opening for accepting axial entry of the distal part 102 by allowing the projections 110 to enter corresponding openings when the proximal part 104 and the distal part 102 are properly aligned. The opening of the grooves 112 are followed by slopes gradually transferring into grooves running along the inner peripheral direction, i.e. defined by a proximal facing surface 115. This arrangement provides a fastening movement between distal and proximal parts 102 and 104 comprising an initial relative axial movement, followed by a combined axial and rotational movement and ending in an exclusive rotational movement.

FIGS. 4a and 4b discloses exploded views of coupling parts of a first embodiment of a medical delivery system according to the present invention. Here, 200 denotes a medical delivery system comprising a container 202 (for simplicity reasons, the distal end of the container has been omitted in the drawing), and a dosing assembly 204 (of which only specific parts related to the distal part is disclosed). The dosing assembly 204 comprises a first fastening means 212 defining a groove for receiving a male member or projection defining a second fastening means 210 provided on the container 202. The groove of the first fastening means 212 defines an opening into which the male member of the second fastening means 210 can be inserted when the container 202 is properly aligned for axial entry into cartridge receiving cavity 250. The container 202 may be fastened to the dosing assembly by advancing the projection into the groove whereby a distal facing surface 211 of the projection (the second fastening means 210) engages a proximal facing surface 215 of the groove (the first fastening means 212). Upon relative rotation between the dosing assembly 204 and the container 202 the two elements are pulled towards each other due to the engagement between the distal facing surface 211 and the proximal facing surface 215. Due to the angular extent of the groove the two elements can only be rotated a limited angle relative to each other i.e. less than one revolution.

In the embodiment shown, the number of distinct pairs of fastening elements 210 and 212 are selected as two. However, the number of distinct pairs of fastening elements 210 and 212 may be selected from 1 to 6. Also, the peripheral distribution of the fastening elements may be organized as evenly distributed along the periphery, or may be distributed unevenly and non-symmetrical.

As in syringe device 100, the medical delivery system 200 may be adapted for coupling container 202 to dosing assembly 204 by a fasteningen sequence comprising an initial relative exclusive axial movement, followed by a combined axial and rotational movement and ending in an exclusive rotational movement. As an alternative, the fastening sequence may comprise a relative axial movement followed by an exclusive rotational movement, i.e. forming a conventional bayonet coupling.

FIG. 4a also shows two spring elements 207 which now will be described in connection with FIG. 4b. The two spring elements 207 are made of spring steel which have been bent or folded to define a hinge section 205. The two spring elements are secured to the dosing assembly 204 in a way that end parts of the spring elements 207 protrudes into a container receiving cavity 250, thereby forming blocking elements 206. Each of the blocking elements 206 are movable from a first unbiased position (the rest position which is shown in FIG. 4b) into a second biased position (not shown) where the blocking elements 206 are moved outwards away from the centre of the container receiving cavity 250. The blocking elements are formed and adapted to resist substantial any movement when forces are exclusively exerted thereon along the axial direction from the distal to the proximal end. In the specific embodiment shown, this is accomplished by dimensioning the blocking elements to be generally stiff and inflexible in the axial direction.

The number of blocking elements in a specific medical delivery system may be selected from 1 to 4 or even more separate blocking elements.

As seen in FIG. 4b, the container 202 is provided with axially indentations 220 that extends from the proximal end of the container in the distal direction. Preferably, the number of axially indentations 220 correspond to the number of blocking elements 206. The angular orientation of axial indentations 220 along the peripheral part of the container 202 relative to the second fastening means 210 of container 202 corresponds to the angular orientation of the blocking elements 206 relative to the openings defined by the first fastening means 212. Thus, when the male members 210 of container 202 is properly aligned with respect to the openings of grooves 212 formed in dosing assembly 204, the indentations 220 are aligned with blocking elements 206.

The indentations 220 of container 202 are adapted to receive the blocking elements 206 when the container is inserted axially into container receiving cavity 250 of dosing assembly 204. In the shown embodiment, when the container has been inserted axially into container receiving cavity, the shape of the indentations 220 or the peripheral dimension of the indentations 220 are adapted to exert a force on the blocking elements when the fastening movement commences the angular movement. Thereby, the wall part of the container positioned next to an indentation exerts a force for moving the blocking elements 207 from the first position and radially outwards responsive to the angular movement of container 202 relative to the dosing assembly 204.

FIG. 4c shows a second variant of the first embodiment of the invention where medical delivery system 200' is adapted to administer a second medicament which is different than the first medicament administerable by medical delivery system 200. Here the relative angular orientation of the indentations 220' with respect to the second fastening means 210' of the container 202' is different than in container 202. As in medical delivery system 200, the orientation of axial indentations 220' along the peripheral part of the container 202' relative to the second fastening means 210' of container 202' corresponds to the angular orientation of the blocking elements 206' relative to the openings of the first fastening means 212'. Consequently, the container 202' is fully axially insertable into container receiving cavity 250' of dosing assembly 204' and also able to be rotated as defined by the specific fastening movement scheme.

In order to prevent mix-up of different container medicaments and non-matching or non-allowed dosing assemblies, containers 202, 202' each having a specific distribution of coding features, e.g. the second fastening means 210, 210' and indentations 220, 220', are dedicated specific coding features according to the medicament contained in each cartridge. Likewise, each dosing assembly 204, 204' is provided with specific corresponding coding features, e.g. first fastening means 212, 212' and blocking elements 206, 206'.

Attempting to insert the container 202' into container receiving cavity 205, the second fastening means 210' of container 202' may be aligned with the openings formed in first fastening means 212 of dosing assembly 204. However, when this condition is fulfilled, it is not possible to align the indentations 220' of container 202' with blocking elements 206 of dosing assembly 204. Due to the blocking elements 206 being able to resist axial directed forces without being moved, the proximal rim part of container 202' will be blocked for axial entry of container 202' into container receiving cavity 250 and, thus, the user will readily acknowledge that container 202' is not the correct type for coupling to the dosing assembly 204. The same conditions apply if the user attempts to insert the container 202 into dosing assembly 204'. Similarly, both of the assemblies 204 and 204' are designed to reject a cartridge holder having no indentations. Also, by correct design of the containers 202 and 202', e.g. the second fastening means 210 and 210', it is assured that neither of the containers 202 and 202' are compatible with a dosing assembly designed to accept a cartridge having no indentations. In this way, a 1-to-1 coding scheme is provided which prevents drug mix-up.

In accordance with the present invention, it is ensured that the coding elements of the container, e.g. the indentations 220, can be designed as relatively narrow axially extending slots and thus provide a sturdy container where the required area reserved for coding purposes are minimized. Also, this design ensures that a large number of distinct codes can be obtained by offering a large number of possible angular positions for the coding elements defined by the indentations 220.

As best seen in FIG. 4a, the container receiving cavity 250 defines an internal peripheral land 240 connecting each of the openings defined by the first fastening means 212. This land 240 provides a guiding surface that the proximal surface part of the second fastening means 210 will be guided against when a user attempts to make an initial rotational alignment of the container 202 with respect to the dosing assembly 204.

The proximal surface part of the second fastening means 210 may be positioned in a distance $X_1$ from the extreme proximal part of the container. In some embodiments of the present invention, this distance $X_1$ is minimized, or ultimately, the proximal surface part of the second fastening means defines the proximal end of the container. By positioning the blocking elements 206, so that the distal part of a blocking element 206 is further away from the land 240 in the proximal direction than the distance $X_1$, it is ensured that the blocking elements 206 cannot be manipulated by the extreme proximal part of the container when a user performs the first initial angular alignment of container 202 and dosing assembly 204. At the same time, the distal part of the blocking elements 206 are preferably positioned so that the blocking elements 206 blocks axial entry of a wrong cartridge before the level is reached where the angular fastening movement commences as defined by the first and second fastening means. Accordingly, indentations 220 of a correct container 202 are designed for full axial insertion into the container receiving cavity 250. However, in observing these requirements, it is preferred that the distal end of the blocking elements 206 are positioned as close as possible to the above described distance $X_1$.

Typically, if the axial extent of the male member forming the second fastening means 210 is defined by the parameter $t_1$, the total axial movement that the container is moved from the point of entry into the first fastening means 212 (which corresponds to the position of the land 240) and towards the fully inserted position is roughly twice the parameter $t_1$ or even more.

When the distal part of the blocking member is arranged in the vicinity of land 240, the indentations 220 preferably has a minimum length of in the order of two times $t_1$. However, if the fastening movement scheme comprises a combined axial and rotational movement, this minimum indentation length may become shorter. Typically, the axial length of the indentation from the proximal end of the container 202 will be longer than $t_1$, and eventually, if the male member of the second fastening means are arranged at a distance from the proximal end of the container, the axial length of the indentations will be longer. Typically, an indentation length will be greater than the parameter $t_1$, such as $t_1$ plus 30%, such as $t_1$ plus 50%, such as $t_1$ plus 100% such as $t_1$ plus 200%, such as $t_1$ plus 300%.

Figure 5:
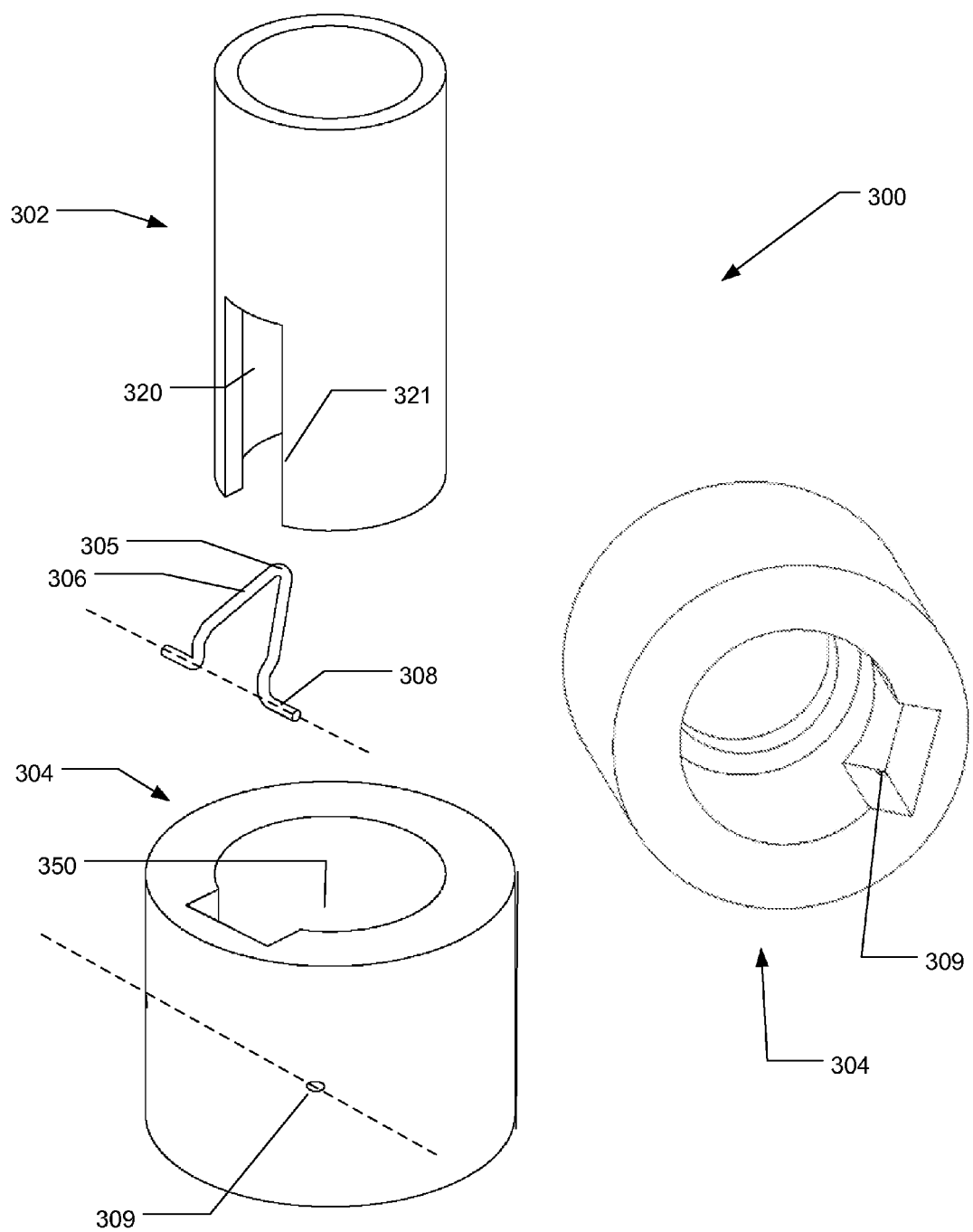

According to a second embodiment of the invention, FIG. 5 shows a medical delivery system 300 having a container 302 and a dosing assembly 304. For simplicity reasons, only the parts related to the flexible coding elements are included. The container 302 is provided with second fastening means and the dosing assembly is provided with corresponding first fastening means. However, those features are not included in the representation shown on FIG. 5. The container generally corresponds to the container described in connection with the first embodiment, thus having one or more indentations 320 for cooperating with blocking elements 306. In this embodiment, the blocking element 306 comprises a piece of bended wire steel having two ends 308 each fitting into a recess 309 in the dosing assembly 304.

When fitted into dosing assembly 304, the element 306 forms a blocking element having a movable part which has a first unbiased position (the rest position which corresponds to the orientation shown in FIG. 5), where the central part of blocking element 305 extends into the container receiving cavity 350 and where the movable part is movable into a second biased position (not shown) where the blocking elements 306 are moved outwards away from the centre of the container receiving cavity 350. The blocking element 306 according to this embodiment generally performs a rotating movement from the first position to the second position around an axis which is transverse to a first longitudinally axis extending through the centre of the pen. The blocking element 306 and the mounting thereof in dosing assembly 304 are formed and adapted to resist substantially any movement of blocking element 306 when forces are exclusively exerted thereon along the axial direction from the distal to the proximal end. In the specific embodiment shown, this is accomplished by dimensioning the blocking element 306 to be generally stiff and inflexible in the pen axial direction. When a container 302, having an indentation 320 conforming to the blocking element 306, is inserted in the container receiving cavity 350, and the container 302 is rotated relative to the dosing assembly, the blocking element 306 or part of the blocking element 306 is forced outwards in a substantial radial direction if a side wall part 321 of the container pass the blocking element 306 during this rotation.

The movement of the blocking element 306 may be limited by additional not shown guide surfaces which prevents the central part of the blocking element 306 to be moved in the proximal direction. This may be accomplished by a not shown part of the dosing assembly, which is situated inside the container receiving cavity 350. Also, the unbiased position may be provided by forming guide surfaces of the dosing assembly 304 to cooperate with the blocking element for forcing the blocking element into its rest position.

Figure 6A:
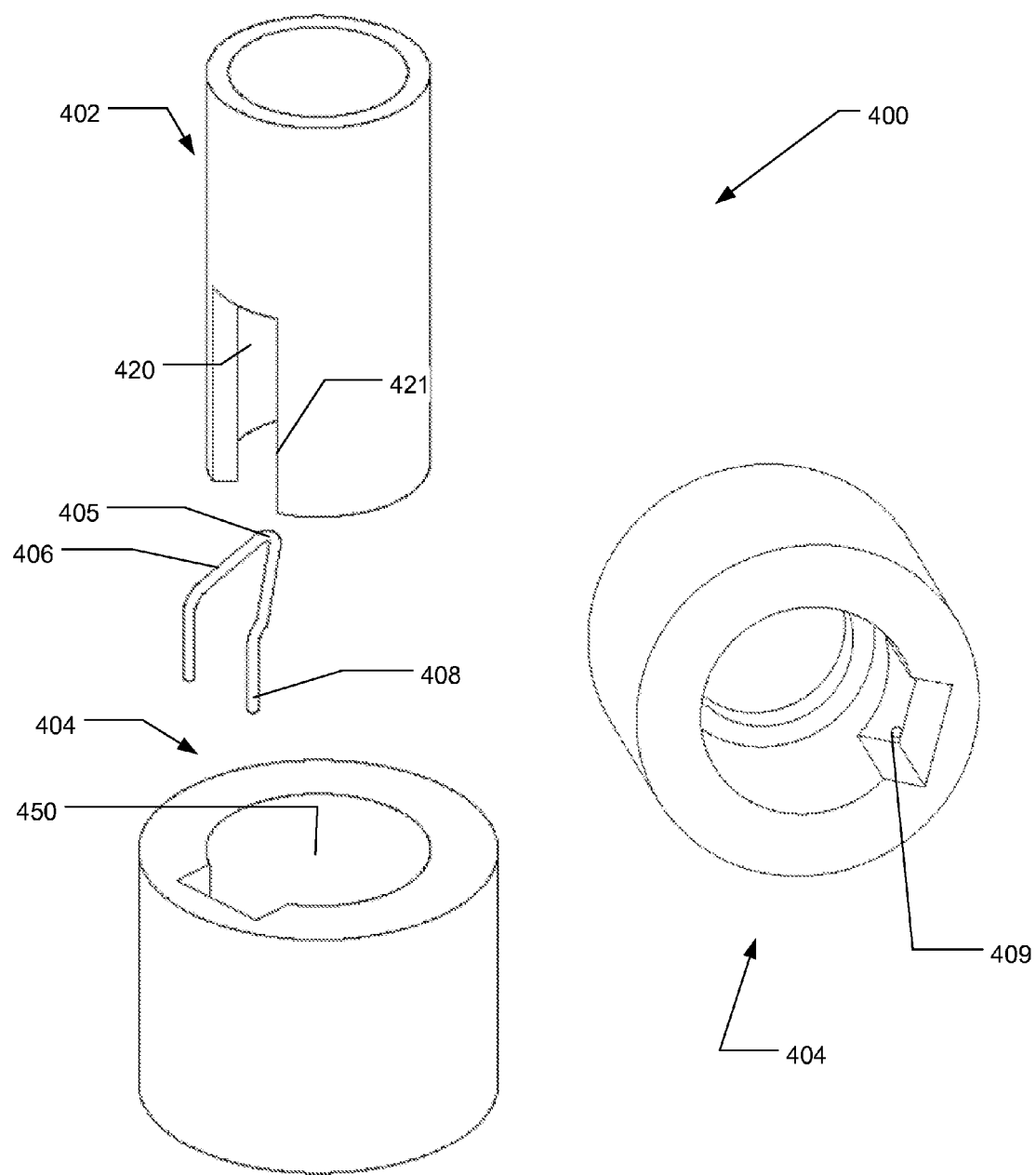
Figures 6B, 6C:
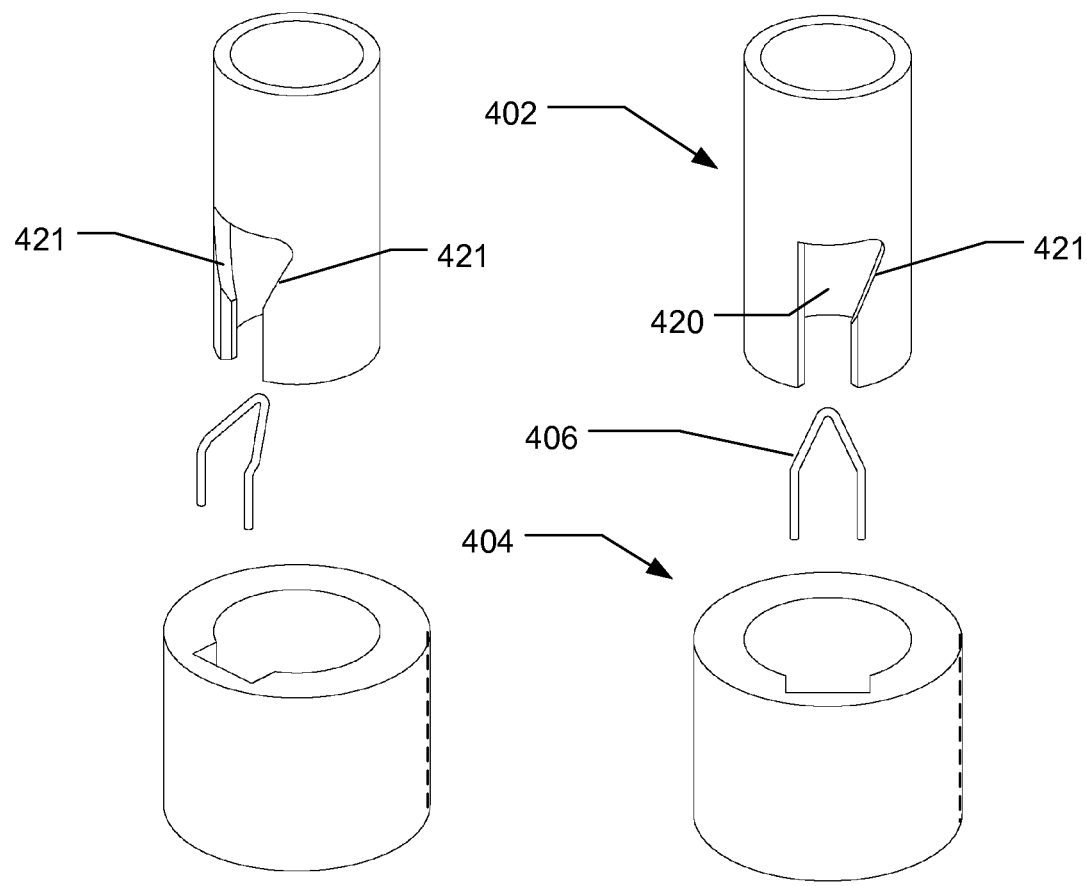

A third embodiment is shown in FIG. 6a, which generally conforms to the concept shown in FIG. 5. Again, the blocking element 406 may be made of bended steel wire. In use, the steel wire has two free ends mountable into recesses 409 extending in the axial direction of the pen. As shown in FIGS. 6b, 6c and 6d, the axial indentations 420 of container 402 may be defined by inclined or curved surfaces facilitating the engagement between a neighbouring side wall part 421 and the blocking element 406 when the side wall part 421 manipulates the blocking element 406 to be moved outwards. The inclined or curved surfaces optimises the contact angle between side wall part 421 and blocking element 406 and, hence, reduces the frictional forces required for rotating the side wall parts 421 past the blocking element 406.

According to the various embodiments of the invention, the indentations 220, 320, 420, 520 of the container may take many different forms which is considered within the scope of the appended claims. Also, the indentations 420 may be formed as openings extending entirely from a central cavity of the container (which is adapted to receive driving means of the dosing assembly 404) and radially outwards towards an external peripheral wall surface of the container 402. Alternatively, according to the specific design of the blocking element 406 and the dosing assembly 404, the indentations do not extend completely from the internal cavity of the container to the exterior wall surface, but may be formed as recessed areas in the wall part thereby forming areas of reduced thickness relative to neighbouring areas.

FIG. 7a-7e shows different embodiments of a container and dosing assembly, the dosing assembly having a blocking element 506 formed as a unitary part of the container receiving portion of the dosing assembly, where the blocking element 506 forms a flexible part allowed to flex along a hinge section defined as a hinge rotating along an axis extending parallel with the central axis of the pen. Alternatively, the blocking element, due to its elastic nature, may be deformed over the entire blocking element section. In the shown embodiment, in order to force the blocking element 506 into its rest position where the central blocking element extends into the container receiving cavity, the flexible member has a spring member 507 attached for exerting an inwardly directed force upon blocking element 506.

Figures 7A, 7B, 7C:
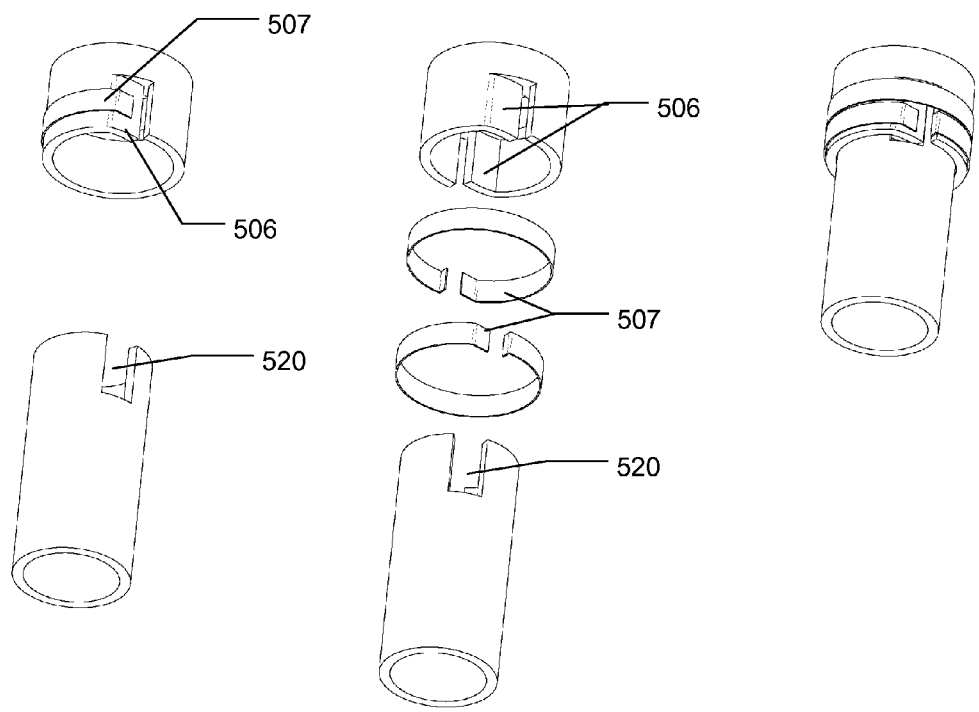
Figure 8A:
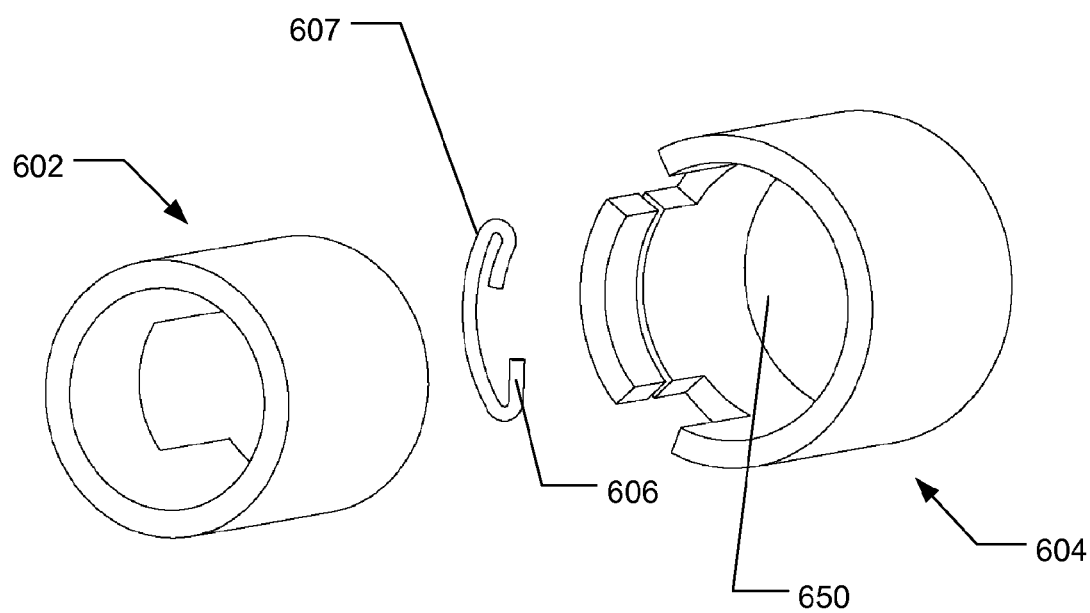
Figure 8B:
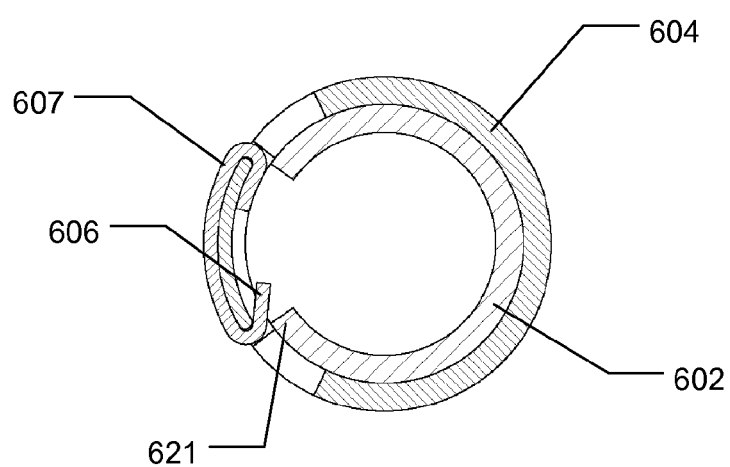

FIG. 7b show a similar construction to the one shown in FIG. 7a, but here two blocking elements 506 arranged around the peripheral section of the container requires corresponding two indentations 520 to be formed in the container for allowing proper coupling. These requirements are met in the depicted embodiment of FIG. 7b. FIG. 7c shows these parts when the container has been fully inserted in container receiving cavity, but before the locking relative rotation has been performed.

Figures 7D, 7E:
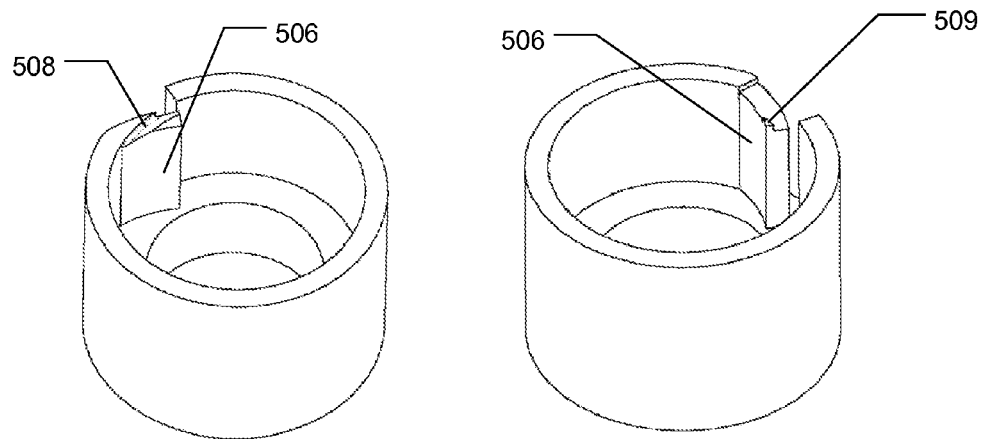

FIGS. 7e and 7d shows specific details a dosing assembly, and more specifically of a distal surface of the blocking element 506. In order to prevent outward movement of the blocking member 506 if a proximal rim part of a container should inadvertently be rotated while contacting the distal surface of the blocking member 506, the blocking member may be provided with a groove 508 into which the rim part of the container may be forced. Alternatively, a protrusion 509 may be formed which is arranged at a smaller distance from the cartridge center than the internal wall face of a container. By these provisions, the blocking member may be locked in its first (rest position) thereby only accepting correct containers.

A further embodiment is shown in FIGS. 8a and 8b where a spring member 607 may be arranged as a blocking member 606. Here the shape of the spring member facilitates correct insertion and retention of the spring member 607 in a groove formed in the dosing assembly. The inherent flexibility of the spring member 607 defines a first position where an end part of the spring member 607 extends into the cartridge receiving cavity. When a container 602 having a matching indentation 620 is rotationally aligned, the container 602 may be moved axially into the container receiving cavity 650 of the dosings assembly 604. This specific state is depicted in FIG. 8b. When the two parts are rotated relative to each other, the flexibility of the blocking member 606 allows the wall part 621 to move past the blocking member 606.

Further not shown embodiments include solutions where the container part of the medical delivery system is provided with one or more flexible members forming blocking members as outlined above. In such configurations, the dosing assembly needs to be equipped with corresponding indentations for the dosing assembly to be assigned to each specific container.

Some preferred embodiments have been shown in the foregoing, but it should be stressed that the invention is not limited to these, but may be embodied in other ways within the subject matter defined in the following claims. The figure e.g. discloses medical delivery systems of the present invention in the form of an injection pen, however, this particular delivery device and its shape is in no way limiting for the present invention as defined in the claims.

The invention claimed is:

1. A medical delivery system comprising:
   a container comprising a housing adapted to contain a medicament in a reservoir and a slideably arranged piston which is moveable in a distal direction towards an outlet so as to reduce the volume of the reservoir and expel the medicament through the outlet;
   a dosing assembly having a container receiving cavity for at least partly receiving the container therein and for coupling the container to the dosing assembly so as to allow driving means of the dosing assembly to move the piston of the container in the distal direction; wherein the dosing assembly defines a first fastening means adapted to engage a second fastening means of the container so as to fasten the container to the dosing assembly where a fastening movement comprises a relative axial movement along a first axis followed by a relative rotational movement around the first axis; wherein the dosing assembly comprises one or more blocking elements, each blocking element being moveable from a first position where the blocking element relative to said first axis extends radially into said container receiving cavity and moveable into a second position where the blocking elements are moved radially outwards, and wherein the blocking elements are moveable from said first position to said second position responsive to said rotational movement while being prevented to move from said first position to said second position when acted upon by an axially directed force; and wherein the container housing, when containing the medicament in said reservoir, defines a proximal end having a second cavity adapted to receive the driving means of the dosing assembly, the proximal end comprising a wall part formed with one or more axially extending indentations, each indentation forming an open area that extends from said second cavity and radially outwards to the container exterior to allow said one or more blocking elements to be received in a respective indentation when the container is axially inserted into said container receiving cavity, and the indentations are moved relatively to the blocking elements responsive to said rotational movement.

2. A medical delivery system as defined in claim 1, wherein the container defines a number of wall parts defining the indentations where at least one wall part are adapted to move a blocking element radially outwards when the container is rotated relative to the dosing assembly.

3. The medical delivery system as defined in claim 1, wherein the blocking elements are swivellably mounted relative to a swivelling axis parallel to said first axis or swivellably mounted along an axis inclined with respect to said swivelling axis.

4. The medical delivery system as defined in claim 1, wherein the blocking elements are flexible elements being substantially inflexible when an axial directed force is exerted on the blocking elements, and wherein the blocking elements are able to flex in radial directions when a force is exerted from a container part being rotated relative to the dosing assembly.

5. The medical delivery system as defined in claim 1, wherein the position of said indentations relative to said second fastening means is dedicated the type of medicament to be contained in said container.

6. The medical delivery system as defined in claim 1, wherein the blocking elements blocks axial entry of a container defined as not allowed, so that the not allowed container is prevented to engage said relative rotational movement.

7. The medical delivery system as defined in claim 1, wherein the second fastening means comprises at least one male mating member defined by a projection extending away from said first axis.

8. The medical delivery system as defined in claim 1, wherein the second fastening means are arranged at the proximal end of said container.

9. The medical delivery system as defined in claim 1, wherein the second fastening means are arranged at the distal end of said container.

10. The medical delivery system as defined in claim 1, wherein the number of said indentations formed in the container are 1, 2, 3, 4 or 5.

11. The medical delivery system as defined in claim 1, wherein the container comprises a plurality of said indentations and where said indentations are distributed irregularly around said first axis.

12. The medical delivery system as defined in claim 1, wherein the container housing comprises a cartridge holder adapted to receive a medicament cartridge.

13. The medical delivery system as defined in claim 1, wherein the fastening movement comprises a purely axial relative movement along a first axis followed by a concurrent relative axial and rotational movement followed by a pure rotational relative movement around said first axis.

14. A container for use with a medical delivery system as defined in claim 1, the container comprising:
   a housing adapted to contain a medicament in a reservoir having an open distal end sealed by a piercable septum and a slideably mounted stopper adapted to be acted upon by driving means of the dosing assembly;
   a proximal end having a second cavity adapted to receive driving means of the dosing assembly;
   second fastening means releasably coupleable to first fastening means of the dosing assembly by a sequence of movements comprising a relative axial movement along a first axis followed by a relative rotational movement around the first axis,
   wherein the second fastening means comprises at least one male mating member having a distally facing surface arranged at a first distance from the proximal end of the container, said distally facing surface fastenable to a corresponding proximal facing surface of the dosing assembly, and
   wherein the container housing, when containing the medicament in said reservoir, defines one or more indentations, where at least one indentation extends from the proximal end of the container a distance in the distal direction greater than said first distance, the indentation forming an open area that extend from said second cavity and radially outwards to the container exterior.

15. A container as defined in claim 14, wherein at least one of said male mating members are defined by a radially extending projection provided at the extreme proximal end of the container.

16. A container as defined in claim 14, wherein at least one of said one or more indentations extends from the proximal end of the container a distance which exceeds said first distance by 50%.

17. A container as defined in claim 14, wherein the container comprises a cartridge holder adapted to receive a medicament cartridge, wherein the cartridge holder proximal end extends beyond the proximal end of the cartridge when the cartridge is inserted therein so that said one or more indentations provides an opening extending from said second cavity and radially outwards to the cartridge holder exterior.

18. A container as defined in claim 14, wherein at least one of said one or more indentations extends from the proximal end of the container a distance which exceeds said first distance by 75%.

19. A container as defined in claim 14, wherein at least one of said one or more indentations extends from the proximal end of the container a distance which exceeds said first distance by 100%.

20. A container as defined in claim 14, wherein at least one of said one or more indentations extends from the proximal end of the container a distance which exceeds said first distance by 150%.

21. A container as defined in claim 14, wherein at least one of said one or more indentations extends from the proximal end of the container a distance which exceeds said first distance by 200%.

22. A container as defined in claim 14, wherein at least one of said one or more indentations extends from the proximal end of the container a distance which exceeds said first distance by 300%.

23. A medical delivery system comprising:
- a container comprising a housing adapted to contain a medicament in a reservoir and a slideably arranged piston which is moveable in a distal direction towards an outlet so as to reduce the volume of the reservoir and expel the medicament through the outlet;
- a dosing assembly having a container receiving cavity for at least partly receiving the container therein and for coupling the container to the dosing assembly so as to allow driving means of the dosing assembly to move the piston of the container in the distal direction; wherein the dosing assembly defines a first fastening means adapted to engage a second fastening means of the container so as to fasten the container to the dosing assembly where a fastening movement comprises a relative axial movement along a first axis followed by a relative rotational movement around the first axis; wherein the dosing assembly comprises one or more blocking elements, each blocking element being moveable from a first position where the blocking element relative to said first axis extends radially into said container receiving cavity and moveable into a second position where the blocking elements are moved radially outwards, and wherein the blocking elements are moveable from said first position to said second position responsive to said rotational movement while being prevented to move from said first position to said second position when acted upon by an axially directed force; and wherein the container housing, when containing the medicament in said reservoir, defines a proximal end having a second cavity adapted to receive the driving means of the dosing assembly, the proximal end comprising a wall part formed with one or more axially extending indentations, each indentation forming an open area that extends from said second cavity and radially outwards to the container exterior to allow said one or more blocking elements to be received in a respective indentation when the container is axially inserted into said container receiving cavity.

* * * * *

UNITED STATES PATENT AND TRADEMARK OFFICE
CERTIFICATE OF CORRECTION

| | | |
|---|---|---|
| PATENT NO. | : 8,579,868 B2 | Page 1 of 1 |
| APPLICATION NO. | : 12/374600 | |
| DATED | : November 12, 2013 | |
| INVENTOR(S) | : Christiansen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Seventh Day of April, 2015

Michelle K. Lee
*Director of the United States Patent and Trademark Office*